United States Patent [19]

Pinhas et al.

[11] 4,011,328
[45] Mar. 8, 1977

[54] DERIVATIVES OF PYRIDINE-3-ACETIC ACID, PROCESS FOR THEIR PREPARATION AND APPLICATIONS THEREOF

[75] Inventors: Henri Pinhas, Paris; Serge Beranger, Bretigny, both of France

[73] Assignee: SERDEX - Societe d'Etudes, de Recherches, de Diffusion et d'Exploitation, Puteaux, France

[22] Filed: Oct. 15, 1974

[21] Appl. No.: 514,778

[30] Foreign Application Priority Data

Oct. 18, 1973 France .............................. 73.37178

[52] U.S. Cl. .................... 424/263; 260/295.5 R; 260/295.5 T
[51] Int. Cl.² ................ A61K 31/44; C07D 213/16
[58] Field of Search ............. 260/295.5 R; 424/263

[56] References Cited

UNITED STATES PATENTS 3,699,227  10/1972  Doyle et al. ..................... 424/263
3,715,358  2/1973   Witzel et al. ..................... 424/263

OTHER PUBLICATIONS

Doyle et al., Chemical Abstracts, 71:38813w (1969).
Doyle et al., Chemical Abstracts, 72:12592u (1970).
Mitchell, Chemical Abstracts, 76:140540v (1972).

*Primary Examiner*—Norman A. Drezin
*Attorney, Agent, or Firm*—Young & Thompson

[57] ABSTRACT

The present invention provides compounds of formula:

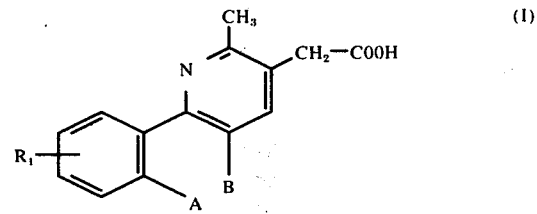

wherein $R_1$ is selected from the group consisting of hydrogen, halogen, alkyl having from 1 to 6 carbon atoms, alcoxy having from 1 to 6 carbon atoms and alkylthio having from 1 to 6 carbon atoms, A taken separately is hydrogen and B is a radical with the formula

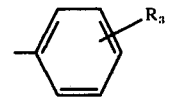

, $R_3$ being selected from the group consisting of hydrogen, halogen and alcoxy having from 1 to 6 carbon atoms, and A and B taken together form a radical —O—CH₂—, and the esters, N oxides and pharmacologically acceptable salts of the acids of Formula I.

These compounds have analgesic and antiinflammatory properties.

10 Claims, No Drawings

DERIVATIVES OF PYRIDINE-3-ACETIC ACID, PROCESS FOR THEIR PREPARATION AND APPLICATIONS THEREOF

The present invention relates to new derivatives of pyridine-3-acetic acid, to a process for their preparation and to their applications, particularly in human medicine.

The new derivatives covered by the invention are in accordance with the following general formula:

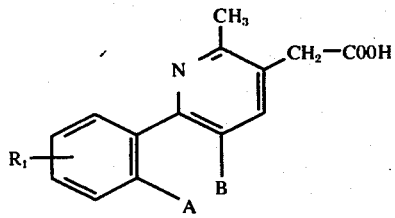

wherein:

$R_1$ represents a hydrogen atom, a halogen atom, an alkyl radical having from 1 to 6 carbon atoms, an alcoxy radical having from 1 to 6 carbon atoms, or an alkylthio radical having from 1 to 6 carbon atoms, A, taken separately, is a hydrogen atom, and B is a radical with the formula

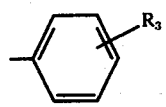

$R_3$ being a hydrogen atom, a halogen atom, an alcoxy radical having from 1 to 6 carbon atoms, or else A and B together form a radical $-O-CH_2-$.

The present invention likewise relates to esters, N oxides and the pharmacologically acceptable salts of the acids of Formula (I).

A preferred class of compounds of formula I are the compounds of formula:

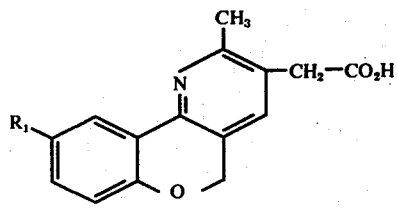

in which $R_1$ is methyl or a halogen atom and their pharmacologically acceptable salts.

Another preferred class of compounds of formula (I) are the compounds of formula

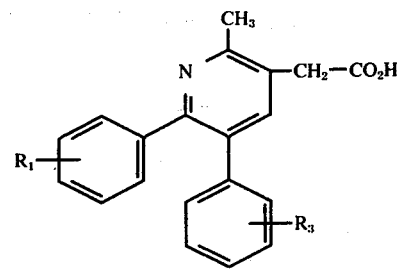

in which $R_1$ is hydrogen, methoxy, methylthio or a halogen atom and $R_3$ is hydrogen, methoxy or a halogen atom and their pharmacologically acceptable salts.

The derivatives of Formula (I) can be prepared by condensation of a dicarbonylated derivative of the formula:

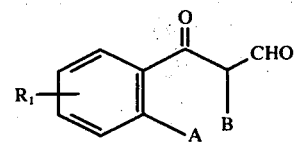

with an animated compound of the formula:

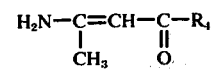

in which $R_4$ represents a radical $O - C_2H_5$ to form a compound of the formula:

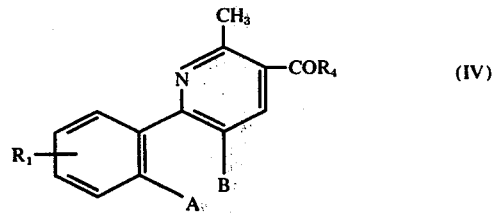

followed by the conversion of the radical $- COR_4$ into a radical $- CH_2- COOH$.

The condensation is advantageously effected in an acid medium, e.g., in an acetic acid medium, using an equimolecular mixture of the dicarbonylated derivative and of the aminated compound.

The conversion of the radical $- COR_4$ into a radical $- CH_2 - COOH$ can be effected by the following schema: $-COOC_2H_5 \rightarrow C-H_2OH \rightarrow CH_2Cl \rightarrow CH_2CH \rightarrow CH_2-COOH$. The compounds of formula (IV) are first of all reduced to primary alcohols by suitable means such as aluminium hydride and lithium hydride, or hydride of sodium-bis(-methoxy ethoxy) aluminium.

The action of the thionyl chloride on these primary alcohols provides the halogenated derivatives. The reaction of the sodium cyanide or potassium cyanide in the dimethyl sulphoxide on these latter derivatives supplies the nitriles, which are converted by hydrolysis into the corresponding acid derivatives.

It is likewise possible to cause a compound of the Formula (IV), in which $R_4$ is $-CH_3$, to react with sulphur and morpholine, in accordance with a Willgerold reaction, in such a way as to convert the radical —COCH₃ into a radical

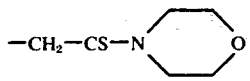

and then to hydrolyse the resulting compound, in such a manner as to obtain the acid desired.

The N-oxide derivatives can be prepared by the action of oxygenated water, in an acetic medium, on the derivatives of the Formula (I).

The initial compounds of Formula (II) can be prepared by the action of ethyl formate on the corresponding ketone, in an alkaline medium.

As regards the compounds of Formula (III), these are already known.

The following examples illustrate the preparation of the compounds according to the invention:

EXAMPLES 1 – 11

The compounds have been prepared according to the following procedure:

a. 0.9 mole of HNa at 57% are placed in suspension in the anhydrous benzene. 0.82 mole of ketone of formula

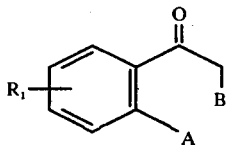

is added, drop by drop, in a nitrogen atmosphere, while cooling to 10°–15° C, in 200 cm³ of dry benzene. 200 cm³ of ethyl formiate is then added in 200 cm³ of benzene and 10 cm³ of methanol. The mixture is shaken, at normal temperature, for 2 hours.

After this period a mixture of ice and water is added. The mixture is decanted and the aqueous phase washed with ether. The organic phases are removed and the aqueous phase acidified by HCl 2 N up to a pH value of 5–6. The mixture is extracted with ether, washed with water, dried, and evaporated in a vacuum.

b. 0.15 mole of the derivative obtained under (a) and 0.2 mole of amino-2-pentene-2-one-4 are dissolved in 90 cm³ of acetic acid and caused to undergo reflux for 48 hours. After cooling, it is evaporated in the dry state, taken up in hydrochloric acid 5 N, extracted with ethyl acetate, and the hydrochloric phase is alkalinized at pH 8, while cooling. The precipitate is dried and recrystallized in hexane or re-distilled.

c. 0.02 mole of the derivative obtained as disclosed under (b), 1.32g of sulphur and 15 cm³ of morpholine are caused to under reflux for 5 hours. The still tepid mixture is poured into the ethanol. Yellow crystals of the thiomorpholino derivative are thus deposited.

d. 12 mmoles of the preceding product are hydrolyzed in 16 hours in a solution of acetic acid and sulphuric acid in water, in a ratio of 120/15/20, in reflux. After cooling, the residue is poured onto ice and alkalinized with potassium carbonate. The solution is washed three times with 50 cm³ of ethyl acetate and acidified to pH 6. The recuperated residue is recrystallized in methanol. The hydrolysis can be effected in a basic medium by boiling for 12 hours in ethanolic potassium. After the evaporation of the alcohol, it is filtered on animal black and acidified by CH₃CO₂H, to a pH of 6. It is extracted with ethyl acetate, dried, and evaporated in the dry state, in a vacuum. The product is recrystallized from the methanol, ethanol, acetone.

The following table defines the compounds I thus prepared and indicates their melting point and also that of the intermediate compounds. These compounds I are in accordance with one or other of the Formulae (Ia) and (Ib), to which reference is made, to enable them to be identified, for the purpose of simplification.

|  | Fusion(melting)point of corresponding compound II. (1) | Fusion(melting)point of corresponding compound IV. | Fusion(melting)point of morpholino-thiocarbonyl-methylated derivative corresponding to compound IV. | Fusion(melting) point of compound Ia or Ib. |
|---|---|---|---|---|
| Ex.1:Compound Ia. $R_1 = -CH_3$ | oil | F = 107° C | F = 219° C | F = 122° C |
| Ex.1:Compound Ia. $R_1 = -Cl$ | F=75° C(120° C) | F = 175° C | F = 206° C | F = 202° C |
| Ex.3:Compound Ib. $R_1 = 4$-OCH₃ $R_3 = 4$-Cl | F=130° C(138° C) | F = 96° C | F = 186° C | F = 150° C |
| Ex.4:Compound Ib. $R_1 = 4$-Cl $R_3 = 4$-Cl. | F=142° C(115° C) | F = 124° C | F = 204° C | F = 140° C |
| Ex.5-Compound Ib. $R_1 = 4$-OCH₃ $R_3 = 4$-OCH₃ | F=138° C(108° C) | F = 98° C | F = 160° C | F = 188° C |
| Ex.6:Compound Ib. $R_1 = 4$-OCH₃ $R_3 = 2$-Cl | Oil (98° C) | Eb₀.₀₃ = 170° C | F = 162° C | F = 190° C |
| Ex.7:Compound Ib. $R_1 = 4$-OCH₃ $R_3 = 4$-F | F=132–135° C (160° C) | F = 90° C | F = 174° C | F = 181° C |
| Ex.8:Compound Ib. $R_1 = 4$-SCH₃ | F=110–112° C | F = 116° C | F = 186° C | F=145–146° C |

-continued

| | Fusion(melting)point of corresponding compound II. (1) | Fusion(melting)point of corresponding compound IV. | Fusion(melting)point of morpholino-thiocarbonyl-methylated derivative corresponding to compound IV. | Fusion(melting) point of compound Ia or Ib. |
|---|---|---|---|---|
| $R_3 = 4$-Cl Ex.9:Compound Ib. | (108° C) | | | |
| $R_1 = 4$-OCH$_3$ $R_3 = H$ Ex.10:Compound Ib. | F=83° C (75° C) | oil | F = 191° C | F = 205° C |
| $R_1 = H$ $R_3 = 4$-Cl Ex.11:Compound Ib. | F:130° C–136° C | F = 134° C | F = 222° C | F = 227° C |
| $R_1 = 4$-Cl $R_3 = H$ | oil (90° C) | oil | F = 210° C | F = 160° C. |

(1) The number in parenthesis indicates the melting point of the ketone from which the compound II is obtained by formylation.

The compounds to which the invention relates are of low toxicity and have anti-inflammatory and analgesic properties.

These properties have been shown in various pharmacological test, as follows:

a. Analgesic power

Siegmend's Test.

(Proc.Soc.Exp.Biol.Med.1957.95.729-31).

The intraperitoneal injection of 0.25 ml of a hydroalcoholic solution of 2-phenyl-1,4-benzoquinone at a concentration of 0.02% produces in mice a particular syndrom characterized by the stretching of the rear feet and the torsion of the trunk.

The test is carried out on homogeneous groups of 20 to 30 mice with an average weight of 20 g.

The substance to be studied is administered to them at the time "0." One hour later the phenylbenzoquinone is administered intraperitoneally. The animals are observed individually for 5 minutes, between the 5th and 10th minute following the injection of the phenyl benzoquinone. The number of stretchings performed by each animal during the observation period is noted.

The percentage of activity of the substance is calculated by comparing the number of torsions performed by the animals and those performed by pilot animals.

b. Anti-inflammatory power.

1. Acute oedema with carragheen.

(Winster C. A., Risley R. A., Nuss G. W. — Proc.-Soc.Biol. Med.1962,3,544-7).

The injection, under the arch of the rat's foot, of 0.05 ml of an aqueous gel with 1% carragheen produces a localized oedema which can be measured with an electric plethysmometer of the mercury type.

The percentage of inflammation can be calculated by measuring the volume of the front foot before and 3 hours after the carragheen injection.

The treatment is given buccally, 1 hour before the carragheen.

The test is carried out on homogeneous groups of ten male rats of 180 ± 10 g.

For each animal the oedema is measured as follows:

$$\frac{Vi - Vo}{Vo} \quad \begin{array}{l} Vi = \text{volume of foot after 3 hrs.} \\ Vo = \text{volume of foot at "time 0."} \end{array}$$

When the percentage of oedema is known for the pilot group, the protection observed under the effect of the substance tested is deducted therefrom for the treated groups.

2. Erythema with Turfyl nicotinate(Trafuril).

The NAINING method is used (Br.jl.Pharmacol. 1963-21-104-12), slightly modified:

The test is carried out on homogeneous groups of six to 12 male albino guinea-pigs weighing 300–400 g, the skin of the back having been carefully plucked the day before.

On the day of the test an antibiogramme disc saturated with an alcoholic solution at 5% of Turfyl nicotinate is applied to the lumbar region for 1 minute.

The result is observed at the end of 5 minutes.

The results are recorded on an "all or nothing" basis, according to which an erythema appears at the place in which the disc was applied.

The treatment is administered buccally 1 hour before the test, with a uniform volume of 1 ml per kg of body weight; the products are placed in homogeneous suspension by the aid of 3% of gum arabic.

The pilot animals are given an equal volume of vehicle.

The percentage of erythema produced in the treated animals is compared with that of the pilot group observed at the same time.

The results obtained are summarized in the following table.

| Ex. | Siegmund | Oedema with carragheen | Trafuril. |
|---|---|---|---|
| 1 | ED$_{50}$ = 150 mg/kg | ED$_{50}$ = 16 mg/kg | ED$_{50}$ = 78 mg/kg |
| 3 | ED$_{50}$ = 0.9 mg/kg | ED$_{50}$ = 28 mg/kg | ED$_{50}$ = 5.2 mg/kg |

The compounds according to the present invention are useful in human therapeutics for the treatment of inflammatory conditions.

Therefore the present invention provides also a process for the treatment of inflammatory conditions which comprises administering to a human a pharmaceutical compound containing a therapeutically effective quantity of a compound according to the present invention.

In such applications the compound is advantageously administered orally on a dosage from 200 to 1000 mg per 24 hours.

Further, the present invention provides also a pharmaceutical composition having analgesic and antiinflammatory activities containing a therapeutically effective quantity of a compound according to the present invention.

This composition may be advantageously administered in an orally administrable form, particularly in the form of tablets, containing 100-250 mg of active principle.

We claim:

1. A compound selected from the group consisting of compounds of the formula:

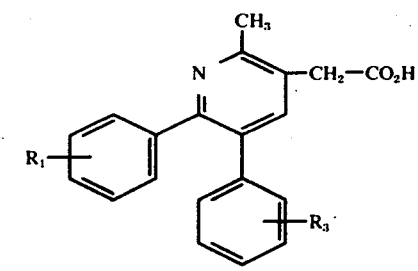

in which R₁ is selected from the group consisting of hydrogen, methoxy, methylthio and halogen and R₃ is selected from the group consisting of hydrogen, methoxy and halogen, and a pharmacologically acceptable salt thereof.

2. A 6-p-methoxyphenyl 5-p-chlorophenyl 2-methyl-pyridine-3-acetic acid and a pharmacologically acceptable salt thereof.

3. 6-p-methoxyphenyl 5-p-fluorophenyl 2-methyl-pyridine-3-acetic acid and a pharmacologically acceptable salt thereof.

4. A pharmaceutical composition having analgesic and anti-inflammatory activities containing an analgesic and anti-inflammatory effective amount of a compound selected from the group consisting of compounds of the formula

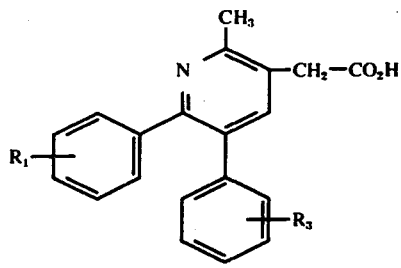

in which R₁ is selected from the group consisting of hydrogen, methoxy, methylthio and halogen and R₃ is selected from the group consisting of hydrogen, methoxy and halogen, and a pharmacologically acceptable salt thereof.

5. A composition as claimed in claim 4, containing an analgesic and anti-inflammatory effective amount of a compound selected from the group consisting of 6-p-methoxyphenyl 5-p-chlorophenyl 2-methyl-pyridine-3-acetic acid and a pharmacologically acceptable salt thereof.

6. A composition as claimed in claim 4, containing an analgesic and anti-inflammatory effective amount of a compound selected from the group consisting of 6-p-methoxyphenyl 5-p-fluorophenyl 2-methyl-pyridine-3-acetic acid and a pharmacologically acceptable salt thereof.

7. A composition as claimed in claim 4 in an orally administrable form containing 100–250 mg of the active principle.

8. A composition as claimed in claim 7, in the form of tablets.

9. A process for the treatment of inflammation which comprises administering to a human in need thereof a pharmaceutical composition containing an analgesic and anti-inflammatory effective amount of a compound selected from the group consisting of a compound selected from the group consisting of compounds of the formula:

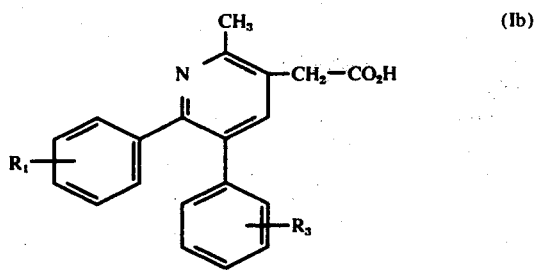

in which R₁ is selected from the group consisting of hydrogen, methoxy, methylthio and halogen and R₃ is selected from the group consisting of hydrogen, methoxy and halogen, and a pharmacologically acceptable salt thereof.

10. A process as claimed in claim 9, which comprises orally administering from 200 to 1000 mg of the compound per 24 hours.

* * * * *